(12) United States Patent
Brusko et al.

(10) Patent No.: US 9,913,830 B2
(45) Date of Patent: Mar. 13, 2018

(54) MATERIALS AND METHODS FOR MODULATING IMMUNE RESPONSES

(75) Inventors: Todd M. Brusko, Gainesville, FL (US); Benjamin G. Keselowsky, Gainesville, FL (US); Judit Cserny, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 176 days.

(21) Appl. No.: 14/241,228

(22) PCT Filed: Sep. 10, 2012

(86) PCT No.: PCT/US2012/054427
§ 371 (c)(1),
(2), (4) Date: May 27, 2014

(87) PCT Pub. No.: WO2013/036914
PCT Pub. Date: Mar. 14, 2013

(65) Prior Publication Data
US 2014/0314866 A1  Oct. 23, 2014

Related U.S. Application Data

(60) Provisional application No. 61/532,209, filed on Sep. 8, 2011.

(51) Int. Cl.
| | |
|---|---|
| *A61K 47/48* | (2006.01) |
| *A61K 31/436* | (2006.01) |
| *A61K 9/51* | (2006.01) |
| *A61K 38/20* | (2006.01) |
| *A61K 38/28* | (2006.01) |
| *A61K 38/51* | (2006.01) |
| *A61K 31/453* | (2006.01) |
| *A61K 31/4704* | (2006.01) |

(52) U.S. Cl.
CPC .......... *A61K 31/436* (2013.01); *A61K 9/5153* (2013.01); *A61K 31/453* (2013.01); *A61K 31/4704* (2013.01); *A61K 38/2013* (2013.01); *A61K 38/28* (2013.01); *A61K 38/51* (2013.01); *A61K 47/48776* (2013.01); *A61K 47/48915* (2013.01); *C12Y 401/01015* (2013.01)

(58) Field of Classification Search
None
See application file for complete search history.

(56) References Cited

U.S. PATENT DOCUMENTS

| | | | |
|---|---|---|---|
| 2005/0186207 A1* | 8/2005 | Bluestone | A61K 39/0008 424/144.1 |
| 2010/0055189 A1 | 3/2010 | Hubbel et al. | |
| 2011/0052529 A1 | 3/2011 | Shirwan | |

FOREIGN PATENT DOCUMENTS

| | | |
|---|---|---|
| WO | WO 2005/070090 A2 | 8/2005 |
| WO | WO 2010 085509 A1 | 7/2010 |

OTHER PUBLICATIONS

Battaglia, Manuela. et al. "Rapamycin Promotes Expansion of Functional CD4+CD25+ FOXP3+ Regulatory T cells of Both Healthy Subjects and Type 1 Diabetic Patients," *The Journal of Immunology*, 2006,177: 8338-8347.
Bluestone, Jeffrey et al. "Therapeutic vaccination using CD4+CD25+antigen-specific regulatory T cells," *PNAS*, 2004, 101:14622-14626.
Brusko, Todd M. et al. "Human Antigen-Specific Regulatory T cells Generated by T Cell Receptor Gene Transfer," *Plos One*, 2010, 5(7):1-12.
Brusko, Todd M. et al. "Human regulatory T cells: role in autoimmune disease and therapeutic opportunities," *Immunological Reviews*, 2008, 223:371-390.
Jonuleit, Helmut. et al. "Infectious Tolerance: Human CD25+ Regulatory T cells Convey suppressor Activity to Conventional CD4+ T helper cells," *Journal of Experimental Medicine*, 2002, 196(2):255-260.
Keselowsky, Benjamin et al. "Multifunctional dendritic cell-targeting polymeric microparticles: Engineering new vaccines for type 1 diabetes," *Human Vaccines*, 2011, 7(1):37-44.
Kohm, Adam et al. "Cutting Edge: CD4+CD25+ Regulatory T cells Suppress Antigen-Specific Autoreactive Immune Response and Central Nervous System Inflammation During Active Autoimmune Encephalomyelitis," *The Journal of Immunology*, 2002,169:4712-4716.
Long, Alice et al. "Defects in IL-2R Signaling Contribute to Diminished Maintenance of FOXP3 Expression in CD4+CD25+ Regulatory T-cells of Type 1 Diabetic Subjects," *Diabetes*, 2010, 59:407-415.
Lowe, Christopher et al. "Large-scale genetic fine mapping and genotype-phenotype associations implicate polymorphism in the IL2RA region in type 1 diabetes," *Nature Genetics*, 2007, 39(9):1074-1082.
Masteller, Emma et al., Expansion of Functional Endogenous Antigen-Specific CD4+CD25+ Regulatory T Cells from Nonobese Diabetic Mice, *The Journal of immunology*, 2005, 175:3053-3059.
Mottet, Christian et al. "Cutting Edge: cure of Colitis by CD4+CD25+ Regulatory T cells," *The Journal of Immunology*, 2003, 170:3939-3943.

(Continued)

*Primary Examiner* — Jake M Vu
(74) *Attorney, Agent, or Firm* — Salwanchik, Lloyd & Eisenschenk

(57) ABSTRACT

The present invention provides nanoparticle-coupled tolerogenic Treg cell therapy for treatment of immune and/or autoimmune disorders. In certain specific embodiments, the present invention can be used in the prevention and/or treatment of autoimmune diseases including, but not limited to, type 1 diabetes, lupus erythematosus (SLE), multiple sclerosis (MS), inflammatory bowel disease (IBD), rheumatoid arthritis, oophoritis, and autoimmune pathology associated with Graft versus Host Disease (GvHD) following hematopoietic stem cell transplantation.

14 Claims, 11 Drawing Sheets

(56) References Cited

OTHER PUBLICATIONS

Polansky, Julia K. et al. "DNA methylation controls Foxp3 gene expression," *European Journal of Immunology*, 2008, 38:1654-1663.

Rieck, Mary et al. "Genetic Variation in PTPN22 Corresponds to Altered Function of T and B Lymphocytes," *The Journal of Immunology*, 2007, 179:4704-4710.

Riley, James et al. "Human T Regulatory Cell Therapy: Take a Billion or So and Call Me in the Morning," *Immunity*, 2009, 30:656-665.

Scalapino, Kenneth J. et al. "Suppression of Disease in New Zealand Black/New Zealand White Lupus-Prone mice by Adoptive transfer of Ex Vivo Expanded Regulatory T cells," *The Journal of Immunology*, 2006, 177:1451-1459.

Setiady, Yulius et al., "Physiologic self antigens rapidly capacitate autoimmune disease-specific polyclonal $CD4^{30}$ $CD25^+$ regulatory T cells," *Blood*, 2006, 107:1056-1062.

Smyth, Deborah et al. "Shared and Distinct Genetic Variants in Type 1 Diabetes and Celiac disease," *The New England Journal of Medicine*, 2008, 359(126):2767-2777.

Tang, Qizhi et al., "In Vitro-expanded Antigen-specific Regulatory T Cells Suppress Autoimmune Diabetes," *The Journal of Experimental Medicine*, 2004, 199(11):1455-1465.

Tsai, Sue et al., "Reversal of Autoimmunity by Boosting Memory-Like Autoregulatory T Cells," *Immunity*, 2010, 32:568-580.

Von Herrath, MG, "Vaccination to prevent type 1 diabetes," *Expert Review Vaccines*, 2002, 1(1): Abstract only.

Wieczorek, Georg. et al. "Quantitative DNA methylation analysis of FOXP3 as a new method for counting regulatory T cells in peripheral blood and solid tissue," *Cancer Research*, 2009,69(2):599-608.

Stephan, Matthias et al., "Therapeutic cell engineering using surface-conjugated synthetic nanoparticles," *Nature Medicine*, Aug. 15, 2010, 16(9):1035-1041.

\* cited by examiner

MATERIALS AND METHODS FOR MODULATING IMMUNE RESPONSES

CROSS-REFERENCE TO RELATED APPLICATION

This application is a National Stage Application of International Application No. PCT/US2012/054427, filed Sep. 10, 2012, which claims the priority benefit of U.S. Provisional Application Ser. No. 61/532,209, filed Sep. 8, 2011 which are incorporated herein by reference in their entirety, including all figures, tables or drawings.

BACKGROUND OF INVENTION

Type 1 diabetes (T1D) arises from a breakdown in immune tolerance, where a chronic autoimmune attack results in the loss of pancreatic β-cells. It is becoming increasing apparent that T1D is associated with immune deficiency, rather than over-reactive immune responses. This is supported by genome-wide association studies (GWAS). For example, T1D patients are more likely to have genetic variants associated with reduced ability to regulate autoreactive T cell responses resulting from defects in T cell receptor (TCR) and aberrant cytokine signaling resulting from genetic defects in CD25, IL2, PTPN2, and PTPN22 (Lowe et al. (2007), Long et al. (2010), Rieck et al. (2007), Smyth et al. (2008)).

Although T1D is a major cause of morbidity and mortality worldwide, current treatment regimes for T1D have achieved only limited success. Immunomodulatory agents that transiently deplete T cells (anti-CD3, Rituximab) have only demonstrated temporary efficacy. Traditional vaccine strategies that involve the administration of autoantigen (e.g., insulin) alone also have failed to adequately block ongoing β-cell auto-immunity. Thus, improved treatment strategies that provide potent and long-term treatment effects are needed.

Regulatory T cells (Tregs) function as a dominant mediator of peripheral immune tolerance. Tregs suppress autoreactive T cell responses via various pathways, including attenuating inflammatory responses induced by antigen presenting cells (APCs) and activating anti-inflammatory biochemical pathways (Brusko et al. (2008)). Tregs create and maintain an anti-inflammatory milieu that fosters the establishment of immunological tolerance. Importantly, this protective effect can be transferred to T cells recognizing de novo antigens through the process of infectious tolerance (Jonuleit et al. (2002)).

Discovering the importance of Tregs in maintaining immune tolerance has opened a new means of therapeutic intervention—adoptive Treg therapy (Riley et al. (2009)). The efficacy of transferred. Tregs as a therapeutic modality has been demonstrated in animal models of systemic lupus erythematosus (SLE) (Scalapino et al. (2006)), multiple sclerosis (MS) (Kohm et al. (2002)), inflammatory bowel disease (IBD) (Nottet et al. (2003)), oophoritis (Setiady et al. (2006)), and T1D (Bluestone et al. (2004), Masteller et al. (2005), Tang et al. (2004)). However, a major limitation of adoptive Treg therapy is the decline of the transferred Treg population. One objective of the present invention is to provide improved adoptive Treg therapy for treating T1D and other immune disorders.

BRIEF SUMMARY

The present invention provides improved adoptive Treg cell therapies for prevention and/or treatment of immune and/or autoimmune disorders, via induction of immune tolerance in a subject. In one embodiment, the present invention provides a nanoparticle-coupled tolerogenic regulatory T cell (Treg) therapeutic composition, comprising:
a) nanoparticles made of bio-degradable material, wherein the nanoparticle encapsulates therein a Treg selective growth factor and an antigen and/or autoantigen;
b) a population of autologous or allogeneic Treg cells; and optionally,
c) one or more additional therapeutic agents of interest; wherein the Treg cells are surface-conjugated with the nanoparticles.

In one embodiment, the nanoparticles of the present invention encapsulate therein a Treg selective growth factor selected from IL-2, rapamycin, and cilostamide.

In certain specific embodiments, the nanoparticle-coupled tolerogenic Treg cell therapeutic compositions can be used in the prevention (such as delaying the onset of the disease), treatment and/or amelioration of an autoimmune diseases including, but not limited to, type 1 diabetes, lupus erythematosus (SLE), multiple sclerosis (MS), inflammatory bowel disease (IBD), and oophoritis. In another embodiment, the nanoparticle-coupled tolerogenic Treg cell therapeutic compositions can be used in the prevention and/or treatment of autoimmune pathologies associated with Graft versus Host Disease (GvHD) following hematopoietic stem cell transplantation.

DETAILED DISCLOSURE

The present invention provides improved adoptive regulatory T cell (Treg) therapy for prevention and/or treatment of immune and/or autoimmune disorders, via induction of immune tolerance in a subject. In one embodiment, the present invention provides nanoparticle-coupled tolerogenic Treg cell therapeutic compositions, comprising:
  a) nanoparticles made of bio-degradable material, wherein the nanoparticle encapsulates therein a Treg selective growth factor and an antigen and/or autoantigen;
  b) a population of autologous or allogeneic Treg cells; and optionally,
  c) one or more additional therapeutic agents of interest; wherein the Treg cells are surface-conjugated with the nanoparticles.

In one embodiment, the nanoparticles encapsulate therein a tolerogenic vaccine composition. As biodegradable NPs release the encapsulated components in a timed fashion, lymph node resident T cells are primed in an antigen-specific and tolerogenic fashion. In one embodiment, the NPs release IL-2 (a Treg selective growth factor) and rapamycin (a mTOR inhibitor) in a timed fashion, thereby skewing T cells toward a regulatory phenotype. In another embodiment, the NPs release IL-2 and cilostamide in a timed fashion, thereby skewing T cells toward a regulatory phenotype. In addition, the present invention provides adoptive Treg therapy using the nanoparticle-coupled tolerogenic Treg cell therapeutic compositions. Advantageously, the present invention achieves antigen-specificity, and is capable of eliciting bystander and infectious tolerance by delivering autoantigens on the surface of autologous Tregs. In addition, the adoptive Treg therapy of the invention can induce durable and long-term tolerance to autoantigens through the process of infectious tolerance.

Figure 1:
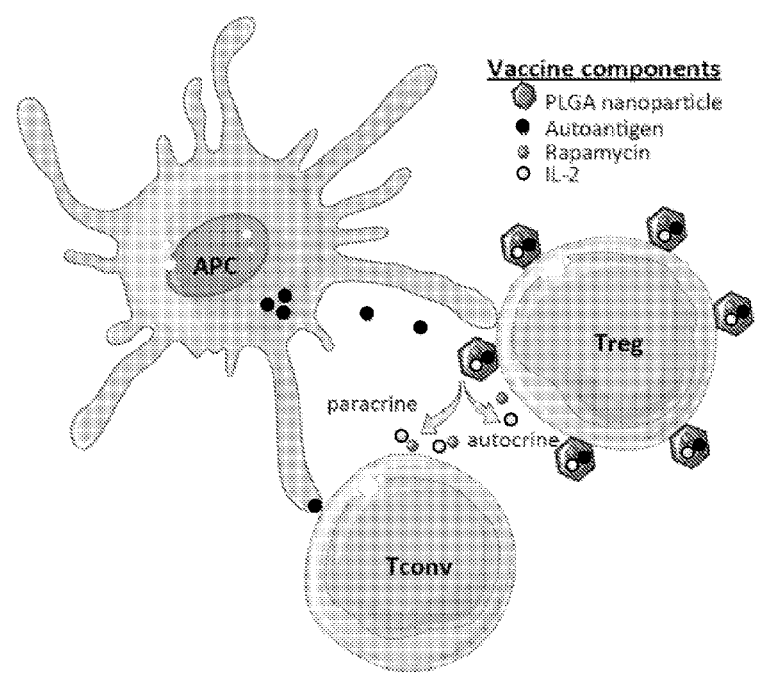
FIG. 1 shows an embodiment of a tolerogenic Treg therapy of the present invention. Briefly, autologous in vitro expanded Tregs are conjugated with vaccine-loaded nanoparticles. NPs are made of poly(lactide-co-glycolic acid) (PLGA)—an FDA approved material commonly used in dissolvable suture material, and have a size of about 300-500 nanometers in diameter. The NPs encapsulate therein therapeutic agents such as Treg selective growth factors (IL-2 and rapamycin) and autoantigenic peptides derived from preproinsulin (e.g., insulin $B_{(9-23)}$). Tregs track to draining lymph nodes, where they create a tolerogenic microenvironment. The vaccine-loaded NPs slowly release the encapsulated therapeutic agents and act in an autocrine and paracrine fashion to induce immune tolerance.
Figure 2:
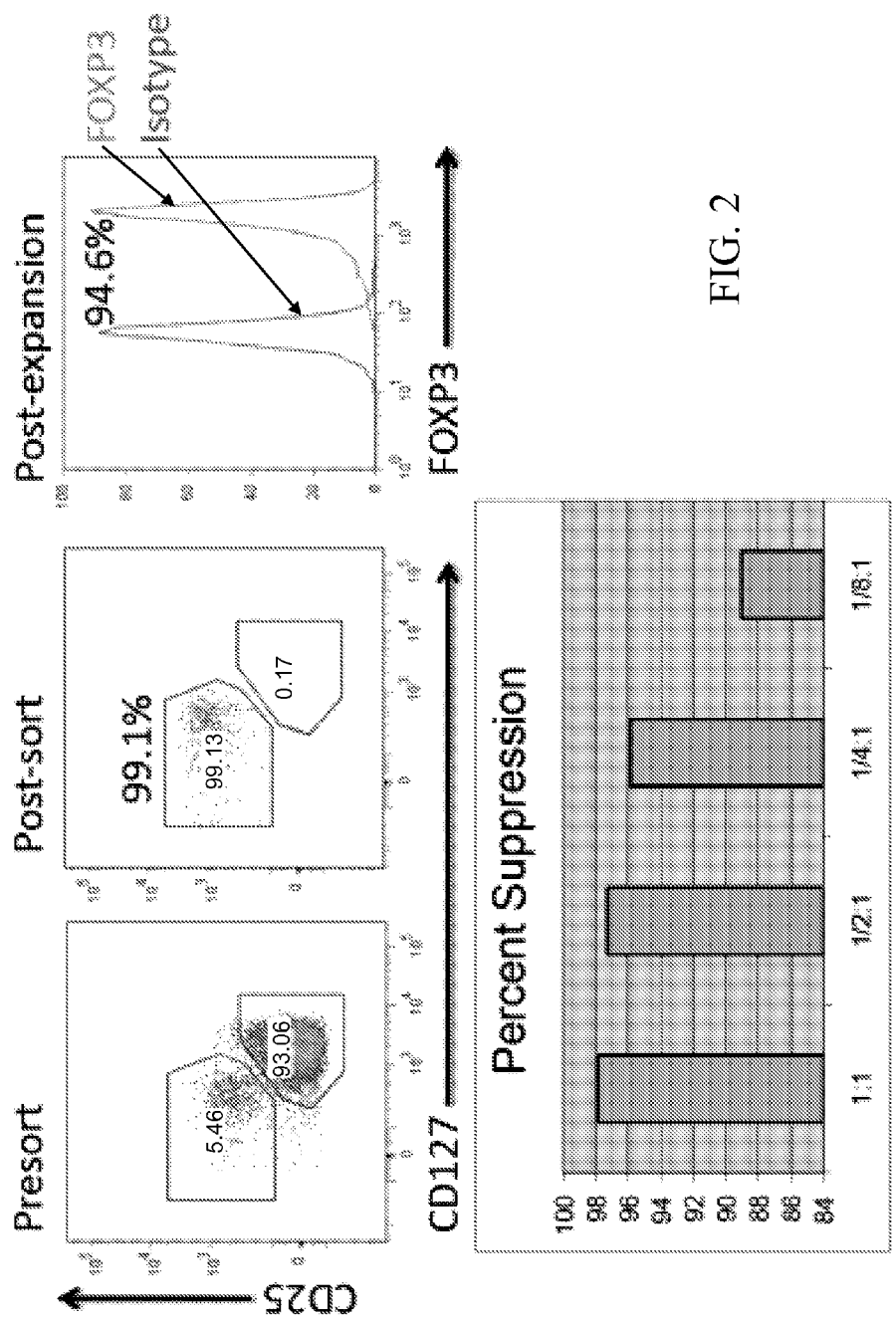
FIG. 2 shows that in vitro expanded human cord blood Tregs suppress the proliferation of CD4$^+$ responder T cells. Briefly, freshly isolated umbilical cord blood CD4$^+$ CD45RA$^+$CD25$^+$CD127$^{31/lo}$ T cells are FACS sorted and expanded for 14 days. Following expansion, cells are analyzed for FOXP3 by FACS and for their capacity to suppress proliferation of CD4$^+$ responder T cells at various ratios of Tregs to Tresp. One representative expansion is shown. Tregs expand an average of 744-fold (n=3) over a 14-day period. The presort panel shows the percentage of Tregs normally present. The post-sort panel shows the percentage following cell isolation and enrichment.
Figure 3A:
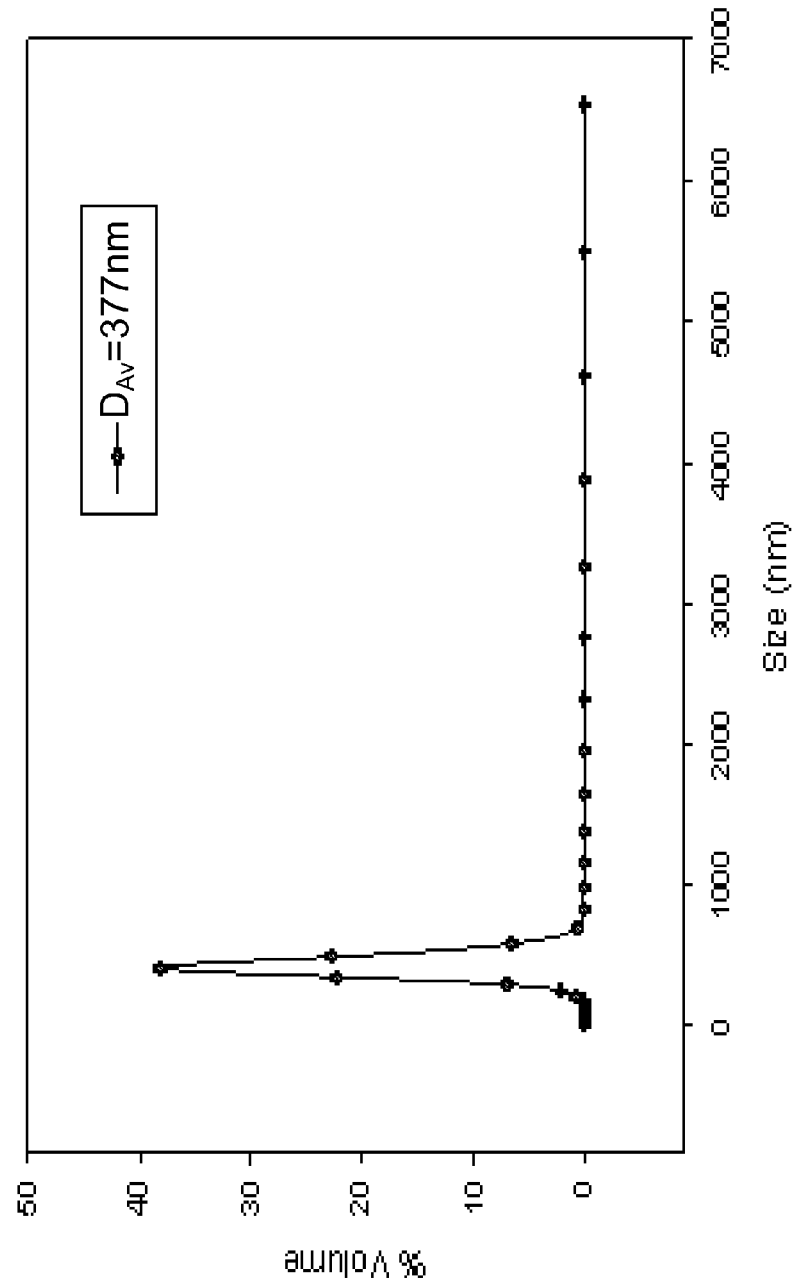
FIG. 3 shows the conjugation of nanoparticles (NPs) to a lymphocyte cell line (BW1100). Briefly, poly(lactide-co-glycolide) nanoparticles (PLGA NPs) are fabricated using water-oil-water double emulsion solvent evaporation technique, yielding a mean NP diameter of 377 nm (histogram). (A) NP diameter is estimated by dynamic light scattering using a volume distribution algorithm. Activated carboxyl groups on the surface of PLGA NPs are conjugated to primary amines present on the surface of BW1100 cells via carbodiimide chemistry. (B) Calcein-loaded BW1100 cells are incubated with either 1-ethyl-3-[3-dimethylaminopropyl]icarbodiimide hydrochloride (EDC)-activated (left panel) or non-activated (right panel) AMCA-loaded NPs for 45 min at 37° C. under gentle agitation. Cells are separated from unbound NPs via gentle washing step. Fluorescence microscopy reveals that EDC-activated NPs selectively bound to the surface of cells.
Figure 3B:
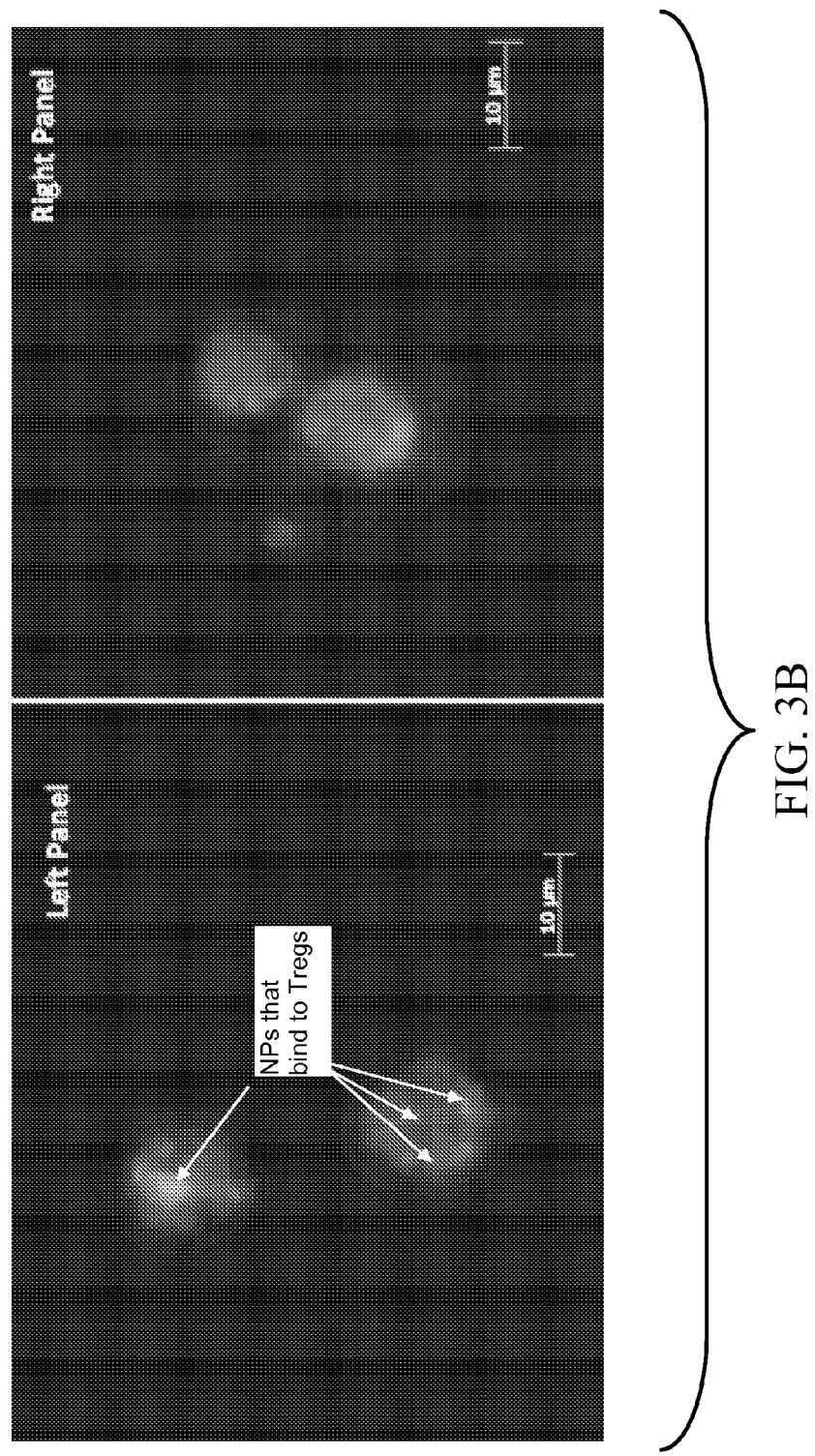

FIG. 1 illustrates one embodiment of the tolerogenic Treg therapy of the present invention. FIG. 2 shows that in vitro expanded human cord blood Tregs suppress the proliferation of CD4+ responder T cells. FIG. 3 shows the conjugation of nanoparticles (NPs) of the present invention to Tregs.

Nanoparticle-Coupled Tolerogenic Treg Cell Therapeutic Composition

In one aspect, the present invention provides nanoparticle-coupled tolerogenic Treg cell therapeutic compositions for treatment of auto-immune disorders such as type 1 diabetes (T1D). In one embodiment, the T-cell therapeutic composition comprises:
  a) nanoparticles made of bio-degradable material, wherein the nanoparticle encapsulates therein a Treg selective growth factor and an antigen and/or autoantigen;
  b) a population of autologous or allogeneic Treg cells; and optionally,
  c) one or more additional therapeutic agents of interest; wherein the Treg cells are surface-conjugated with the nanoparticles.

Preferably, the nanoparticle matrix is made of, primarily, substantially biologically inert or biologically compatible materials. The terms "inert," "biologically inert" or "biologically compatible," as used herein, refer to a substance or material that, after the normal healing period when administered into living tissues, does not elicit substantially adverse biochemical, allergic, or unwanted immune responses.

Biocompatible materials useful for making the nanoparticles include, but are not limited to, bio-degradable polymeric materials including, but not limited to, hydrogel, collagen, alginate, poly(glycolide) (PGA), poly(L-lactide) (PLA), poly(lactide-co-glycolide) (PLGA), polyethylene glycol (PEG), polyesters, polyanhydrides, polyorthoesters, polyamides; non-polymeric biodegradable ceramic materials including, but not limited to, calcium phosphate, hydroxyapatite, tricalcium phosphate; or a combination thereof.

In a preferred embodiment, the nanoparticles are fabricated from poly(lactic-co-glycolic acid) (PLGA), which is FDA approved for delivery of therapeutics.

In one embodiment, the outer surface of the nanoparticle comprises one or more surface ligands or surface antibodies that bind to Treg cells.

In one embodiment, the outer surface of the nanoparticles is covalently linked to the surface of Treg cells. In a specific embodiment, the outer surface of the nanoparticles comprises activated carboxyl groups, which can be conjugated to primary amines present on the surface of Treg cells. In one embodiment, the conjugation of nanoparticles to Tregs is facilitated by 1-ethyl-3-[3-dimethylaminopropyl]carbodiimide hydrochloride (EDC) and/or N-hydroxysulfosuccinimide (NHS), or in an alternative embodiment using a malemide thiol linker.

In specific embodiments, the Treg selective growth factor is IL-2, rapamycin or a phosphodiesterase (PDE) inhibitor including, but not limited to, cilostamide, theophylline, pentoxifylline, zaprinast, sildenafil, arninone, milrinone, rolipram, and cilomilast. In one embodiment, the Treg selective growth factor is a phosphodiesterase 3B (PDE3b) inhibitor such as cilostamide. IL-2 is a Treg selective growth and survival factor.

The antigen and/or auto-antigen (associated with an autoimmune disease) useful according to the present invention can be derived from endogenous antigenic peptides or peptide fragments capable of inducing autoreactive and regulatory responses.

In the case of diabetes, the autoantigens useful according to the present invention can be, for example, insulin, islet cell autoantigen, glutamic acid decarboxylase (GAD), and insulinoma-associated-2-protein (IA-2). In a specific embodiment, the autoantigen for treatment of T1D is derived from preproinsulin (e.g., insulin $B_{(9-23)}$ peptide).

In certain embodiments, therapeutic agents include, for example, immunomodulatory agents, transforming growth factor beta 1, vitamin D, and retinoic acid; anti-inflammatory agents including, but not limited to, hemoglobin:haptoglobin, hemin, heme:hemopexin, nonsteroidal anti-inflammatory drugs (NSAIDs) such as aspirin, ibuprofen, and naproxen, triterpinoids such as betulinic acid, bardoxolone methyl, and triterpenoid saponins, ethyl pyruvate (EP), hemeoxygenase (HO-1)-pathway activators, arachidonic acid-pathway inhibitors, and COX-pathway inhibitors; immune-regulatory cytokines including, but not limited to, IL-10 and TGF-β.

In certain embodiments, the nanoparticles have a diameter ranging from 10-1000 nm, or any values therebetween, such as 50-900 nm, 100-800 nm, 200-500 nm, 300-400 nm, etc. In preferred embodiments, the nanoparticles have a diameter from 300 nm to 500 nm, or any values therebetween, such as 300-450 nm, 300-400 nm, 330-480 nm, 350-450 nm, 350-400 nm, etc.

In one embodiment, the Treg cells are isolated from umbilical cord blood or peripheral blood cells. In another embodiment, in vitro expanded Treg cells from human peripheral blood are used. In certain embodiments, the Treg cells are $CD45RA^+CD25^+CD127^{-/lo}$ cells.

The Treg cells useful according to the present invention can be Treg cells of various species including, but not limited to primates such as human, apes, chimpanzees, orangutans, monkeys; animals such as dogs, cats, horses, cattle, pigs, sheep, goats, chickens, mice, rats, guinea pigs, and hamsters. In a preferred embodiment, human Treg cells are used.

In one embodiment, the T-cell therapeutic composition comprises:
a) nanoparticles made of bio-degradable material, wherein the nanoparticle encapsulates therein a Treg selective growth factor and an antigen and/or autoantigen; and optionally,
b) a population of autologous or allogeneic Treg cells; and
c) one or more additional therapeutic agents of interest; wherein the nanoparticles are capable of conjugation to the surface of Treg cells.

Treatment of Immune Disorders and/or Autoimmune Diseases

The present invention provides improved adoptive Treg cell therapy for inducing immune tolerance in a subject. The method comprises administering to the subject: autologous Treg cells that are surface-conjugated with nanoparticles. In one embodiment, the nanoparticles are made of bio-degradable polymeric material and the nanoparticle encapsulates therein a Treg selective growth factor and an autoantigen, and the surface of said nanoparticle binds to a Treg cell surface.

In another embodiment, the present invention provides a method for inducing immune tolerance in a subject, wherein the method comprises administering to the subject a T-cell therapeutic composition comprising:
a) nanoparticles made of bio-degradable material, wherein the nanoparticle encapsulates therein a Treg selective growth factor and an antigen and/or autoantigen; and optionally,
b) a population of autologous or allogeneic Treg cells; and
c) one or more additional therapeutic agents of interest; wherein the nanoparticles are capable of conjugation to the surface of Treg cells. The adoptive Treg cell therapy of the present invention can be used to prevent, treat, or ameliorate immune disorders and/or autoimmune diseases.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof. The term "prevention" or "treatment," as used herein, does not mean that complete elimination of symptoms of the disease or disorder must occur.

The term "effective amount," as used herein, refers to an amount that is capable of treating or ameliorating a disease or condition or otherwise capable of producing an intended therapeutic effect.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters.

In one embodiment, the T-cell therapeutic composition of the present invention is administered to a subject having a family history of, or other factor indicative of a predisposition for developing an autoimmune disease or immune disorder. Many autoimmune diseases, including type 1 diabetes, are considered to be caused by a combination of genetic and environmental factors. If an autoimmune disease is present in a family, other relatives may be at risk of developing the same autoimmune disease, or a different autoimmune disease. Certain environmental factors also play a role in instigating autoimmune processes. For example, drugs such as procainamide and hydrolyzine can induce a lupus-like syndrome in genetically-susceptible individuals that remits when the drug is discontinued. Other drug-induced autoimmune diseases have been described, including some of the hemolytic anemias, thrombocytopenias, and the leukopenias. In one embodiment, the present invention can be used in the prevention, treatment or amelioration of immune disorders and/or autoimmune diseases, particularly, type 1 diabetes. In certain embodiments, the present invention is useful to treat or ameliorate immune disorders and autoimmune diseases including, but not limited to, type 1 diabetes, rheumatoid arthritis, celiac disease, pemphigus vulgaris, and the prototype for autoimmune disease, systemic lupus erythematosus (SLE) and related disorders, in which the induction of antigen-specific immune tolerance and/or suppression of over-reactive immunity or auto-immunity is beneficial. In another embodiment, the present invention can be used in the prevention, treatment or amelioration of autoimmune pathologies associated with Graft versus Host Disease (GvHD) following hematopoietic stem cell transplantation.

In certain specific embodiments, the present invention can be used in the prevention, treatment or amelioration of autoimmune diseases including, but not limited to, type 1 diabetes, lupus erythematosus (SLE), multiple sclerosis (MS), inflammatory bowel disease (IBD), and oophoritis.

In addition, the present invention can be used in the prevention, treatment or amelioration of infection, inflammation, allergenic reactions, diseases associated with cell proliferation, angiogenesis, and malignancy.

Formulations

The present invention provides for therapeutic or pharmaceutical compositions. Suitable non-toxic pharmaceutically acceptable carriers for use with the agent will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985).

In one embodiment, the nanoparticles of the present are formulated into a vaccine composition for administration to a subject who is at risk for developing inflammatory and/or autoimmune-related disorders. A vaccine composition is an antigenic preparation that comprises one or more immunogenic antigens used to produce active immunity to a disease. In addition, the compositions of the present invention can be administered to a subject with existing symptoms of one or more inflammatory and autoimmune-related disorders, and provides for customized administration schedules and compositions to prevent or minimize worsening of the disease(s).

The therapeutic dosage range can be determined by one skilled in the art having the benefit of the current disclosure. Naturally, such therapeutic dosage ranges will vary with the size, species and physical condition of the patient, the severity of the patient's medical condition, the particular dosage form employed, the route of administration and the like.

The composition can be administered in a single dose or in more than one dose over a period of time to confer the desired effect.

The carrier can be a solvent or dispersion medium containing, for example, water, ethanol, polyol (for example, glycerol, propylene glycol, and liquid polyethylene glycol, and the like), dimethylsulfoxide (DMSO), suitable mixtures thereof, and vegetable oils. The proper fluidity can be maintained, for example, by the use of a coating, such as lecithin, by the maintenance of the required particle size in the case of dispersion and by the use of surfactants.

EXAMPLES

Following are examples that illustrate procedures for practicing the invention. These examples should not be construed as limiting. All percentages are by weight and all solvent mixture proportions are by volume unless otherwise noted.

Example 1—Generation of Nanoparticles Loaded with Autoantigens and Regulatory T Cell Growth Factors Nanoparticles are fabricated from the FDA approved suture biomaterial PLGA, the copolymer of lactic and glycolic acid in a 50:50 ratio. For encapsulation of the regulatory T cell (Treg) growth factor IL-2, the double-emulsion solvent evaporation method is used. The double-emulsion solvent preparation method is suitable for encapsulating hydrophilic molecules. For encapsulation of rapamycin, which enhances and stabilizes a Treg phenotype and is poorly soluble in water, the single emulsion method is used.

Nanoparticles (NP) having a diameter of approximately 300-500 nm are fabricated. Particle size and quality can be controlled by various factors, including input energy, the amount of surfactant present when forming the emulsion, humidity, the size of the droplets when injecting the aqueous phases into the organic phase, and the ratio of the organic phase to the outer aqueous phase. The primary factors for controlling particle size and quality are the input energy and the amount of surfactant in the reaction that coats the particles' surface.

In the process of fabricating the nanoparticles, the two primary variables, the input energy and the amount of surfactant, are modulated. In one embodiment, the main source of energy is homogenization; also, the input energy is affected by, to a lesser extent, the stirring rate during emulsification. Therefore, the speed and duration of homogenization have significant impact on the particle size.

Figure 4A:
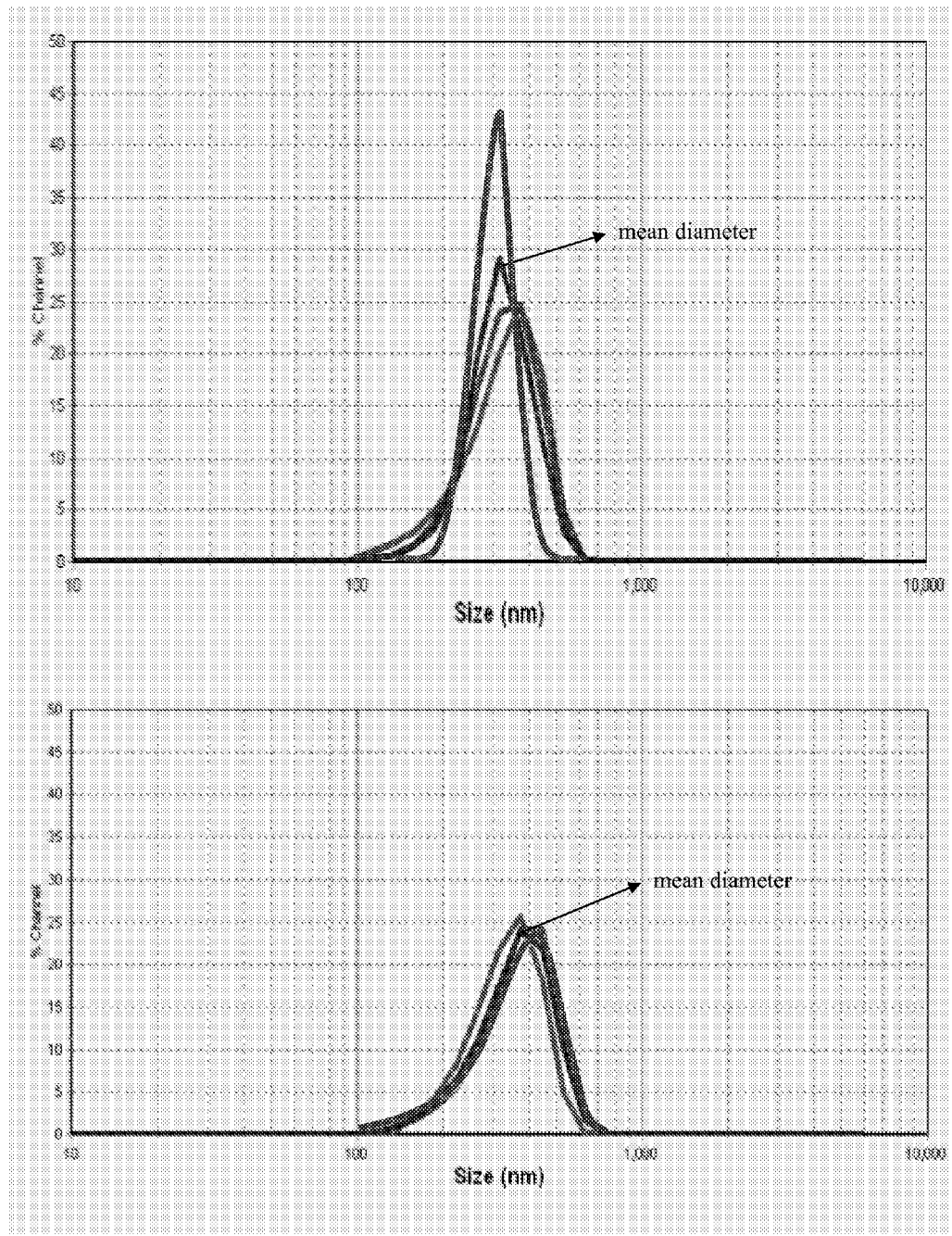
FIG. 4 shows characterization of nanoparticles (NPs) made of PLGA. (A) shows representative histogram of NP diameter using the dynamic light scattering (DLS) method. Comparison plot shows three runs (histogram overlays; red, green, yellow) and the mean diameter (blue). NPs are prepared by double-emulsion method, using propylene carbonate (PC) (top) and methylane chloride (MC) (bottom) as organic solvents. In both formulations 10% polyvinyl alcohol (PVA) is used for both aqueous phases. (B) shows an image of Qdot-loaded NP (ex/em 705/750) by fluorescent microscope, 20× magnification. (C) shows scanning electron micrograph image of NPs in $H_2O$ (1.0 kV, ×4.0K magnification).
Figure 4B:
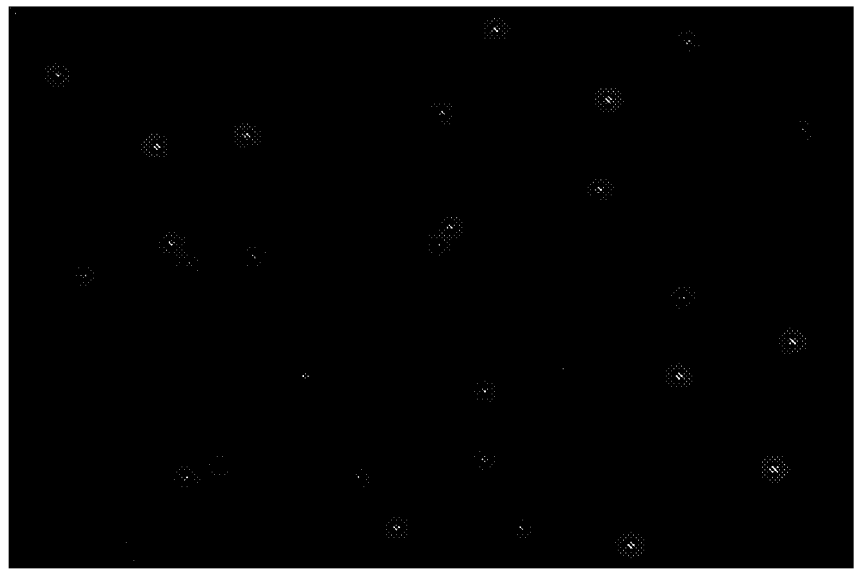
Figure 4C:
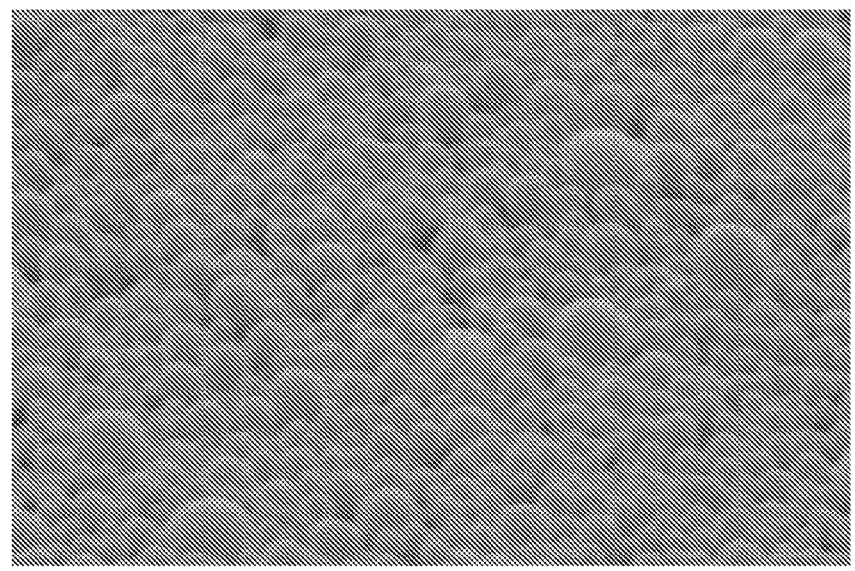

As shown in Table 1, Formulation 2 yields the smallest NP diameter and the narrowest size range, as determined by dynamic light scattering (DLS) (FIG. 4A). In the presence of high concentrations of PVA, the yield and quality of the particles are significantly compromised due to particle aggregation. In another experiment, Formula 3 is used and results in the least amount of particle aggregation.

TABLE 1

| Formulation No. | Organic solvent | W1 PVA % | W2 PVA % | Homogenization time | Mean NP diameter (V) (nm) |
|---|---|---|---|---|---|
| 1 | PC | 5 | 10 | 2 | 359.0 |
| 2 | PC | 10 | 10 | 2 | 279.0 |
| 3 | MC | 5 | 5 | 2 | 507.0 |
| 4 | MC | 10 | 10 | 2 | 413.0 |

Table 1 shows a summary of various formulations used for NP fabrication. Homogenization speed is 15,000 rpm for all formulations. PC=propylene carbonate, MC=methylene chloride, PVA=polyvinyl alcohol.

Figure 5A:
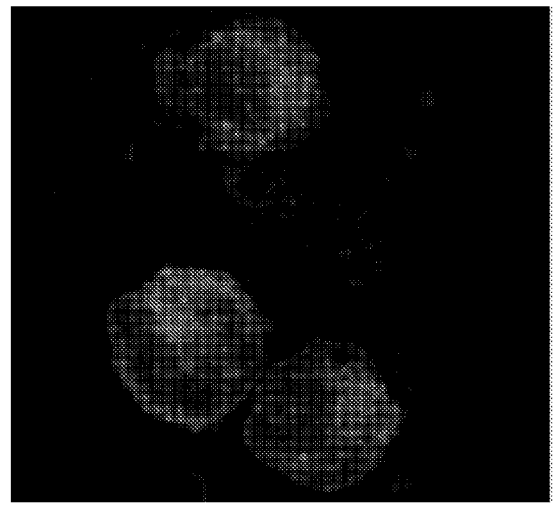
FIG. 5 shows that NPs are convalently conjugated to Jurkat T cells in culture. (A) NPs, loaded with AmCyan dye (Ex-Max 457 nm/Em-Max 491 nm), are crosslinked using a PEG-malemide linker or PEG-methyl (negative control) to SIGMA-PKH26 membrane-stained Jurkat cells and imaged by confocal microscopy. (B) Fluorescence of crosslinked NPs is measured from day 0 to day 5 following conjugation. (C) NP coupled cells are visualized by AMNIS® Imaging Flow Cytometry (60×) using Coumarin-6-loaded NPs (ex/em 450/520).
Figure 5B:
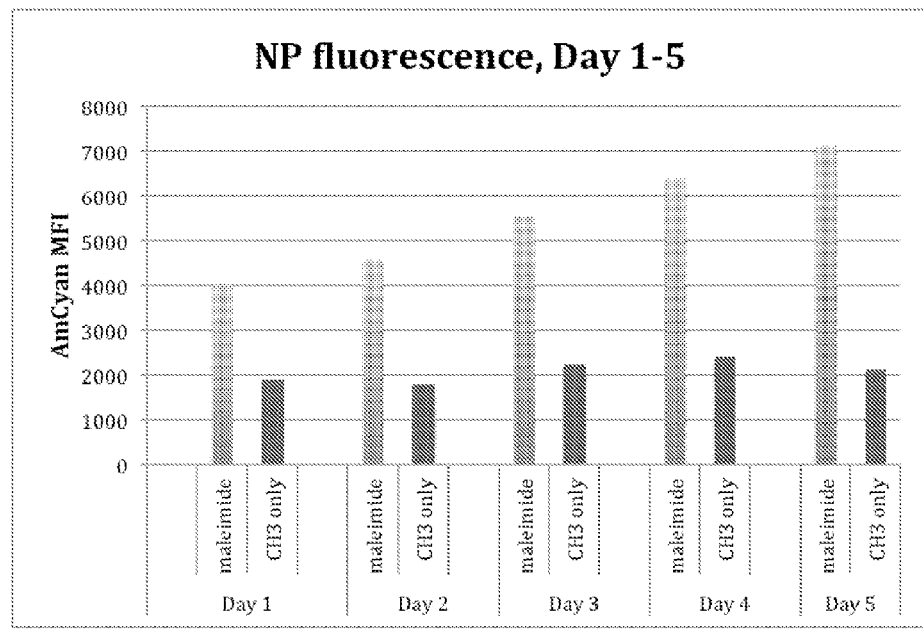
Figure 5C:
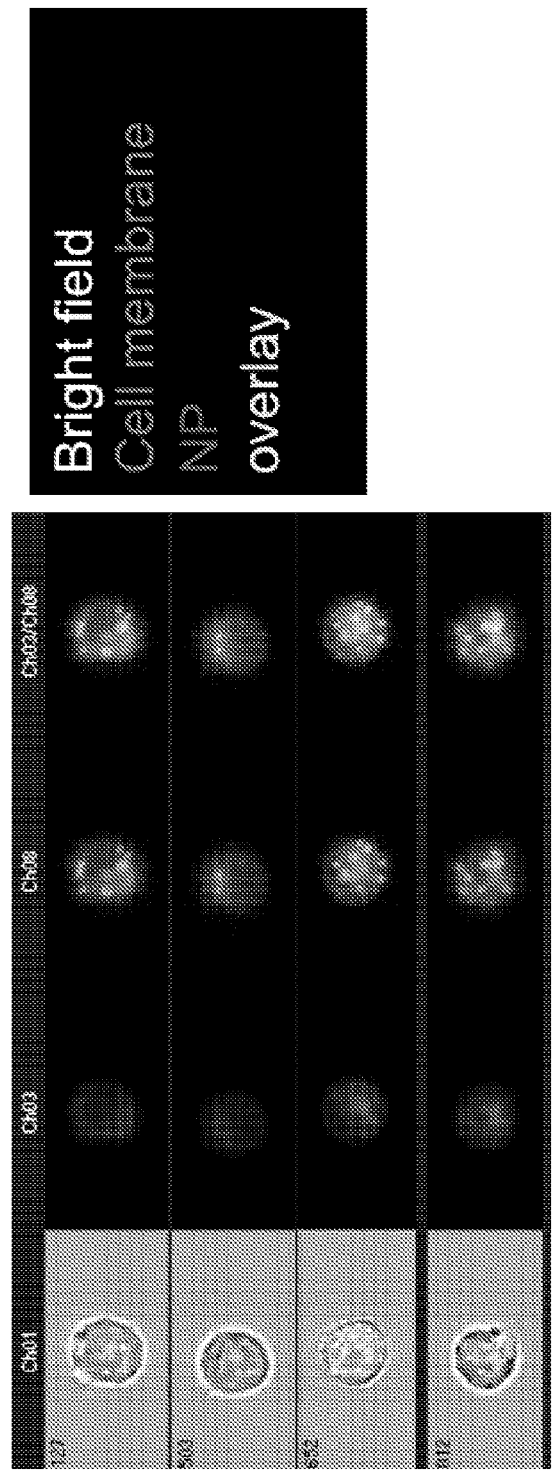

Example 2—Development and Optimization of the Conjugation of Nanoparticles to In Vitro Expanded Regulatory T Cells and In Vitro Activity of Nanoparticle-Conjugated Cells Various approaches can be used for conjugating nanoparticles (NPs) to T cells. In one embodiment, an amide bond can be formed between a carboxyl group of PLGA and a primary amine of any cell surface protein with the aid of 1-ethyl-3-[3-dimethylaminopropyl]carbodiimide hydrochloride (EDC) and N-hydroxysulfosuccinimide (NHS), which facilitate the formation and stablization of the amine-reactive ester intermediate. Briefly, NPs are stably conjugated to Jurkat cells, a T cell lymphoma cell line, via the formation of a stable covalent bond (FIG. 5A). The NP-conjugated Jurkat cell particles are detectable six days after conjugation (FIG. 5B). In another embodiment, a cross-linker, polyethylene glycol (PEG)-maleimide, which reacts with free sulfhydryl groups on the cell surface, can be used. This reaction resulted in fewer cross-linked particles per cell (FIG. 5C).

In this Example, a stable amide bond is formed when cells are incubated with nanoparticles, previously activated by EDC and NHS with gentle rocking. Conjugation efficiency is influenced by a number of factors, including incubation time and volume as well as by the NP to cell ratio. Therefore, the direct conjugation process can be optimized in order to achieve maximum efficiency without compromising cell viability.

Figure 6:
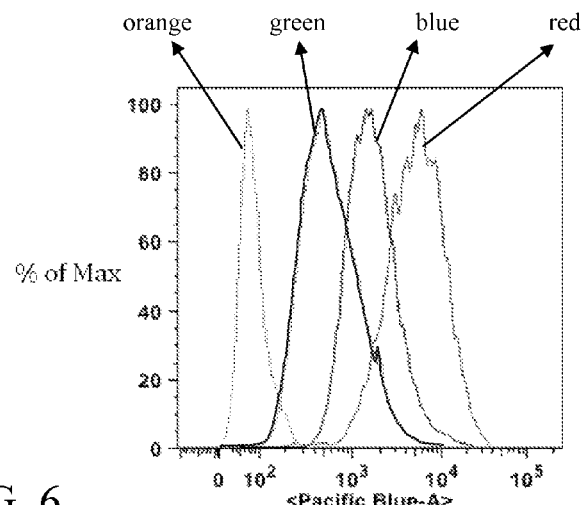
FIG. 6 shows that IL-2 loaded NPs induce proliferation of CTLL-2 cells. IL-2 loaded particles are conjugated to CTLL-2 cells, and are stained with Cell Trace Violet dye. Cell proliferation is assessed based on the dilution of the dye 7 days post-conjugation. Histogram overlays shows: Blue=IL-2 NP conjugated CTLL-2 cells; Red=Blank NP+CTLL-2 cells; Orange=unstained control; Green=soluble IL-2 supplemented control (200 IU/ml).

As shown in FIG. 6, IL-2 loaded NPs facilitate T cell growth and persistence. To assess the bioactivity and the growth properties of cytokine-loaded NPs on T cells, IL-2 loaded particles (IL-2 NP) are conjugated to CTLL-2 cells from an IL-2 dependent mouse T cell line. Cells with IL-2 loaded NPs conjugated on the cell surface exhibit greater level of proliferation than cells conjugated with empty nanoparticles or cells that are not conjugated with nanoparticles. In addition cells conjugated with IL-2 loaded NPs show higher expression levels of CD25. CD25 is an α-subunit of the IL-2R, and is upregulated in response to IL-2 signaling (FIG. 6).

Example 3—Prevention and Treatment of Diabetes in the Non-Obese Diabetic (NOD) Mouse By Administration of NP-Coupled Regulatory T Cells This Example identifies selective immunosuppressive agents that can be used to preserve regulatory T cells (Tregs) stability and to elicit a regulatory phenotype in conventional T cells. In addition, this Example improves adoptive transfer of Treg by co-administering small molecules in NPs to support and induce the regulatory phenotype.

Rapamycin, an mTOR inhibitor, has been shown to induce and expand Treg population. It inhibits the mTOR-Akt pathway, and, thus, results in the Akt-mediated inhibition of Foxo proteins. Foxo proteins are required for FOXP3 induction, which is the most important mediator of the suppressive function of Treg. The mTOR-akt pathway is also required for cell survival and proliferation; therefore, downregulating the mTOR-akt pathway induces FOXP3 but impairs Treg expansion.

Cilostamide enhances the regulatory phenotype without halting Treg proliferation upon cell transfer; therefore, cilostamide can be a useful for induction of a regulatory phenotype in transplantation settings.

Tregs have high levels of cAMP, which is transferred to effector T cells (Teffs) via gap junctions in a contact-dependent manner. Upon transfer, cAMP regulates cell proliferation and cytokine production in target cells, and this process constitutes one mechanism of Treg suppressive function. cAMP level is controlled by the balance between the conversion of ATP into cAMP by adenylyl cylcase (AC) and its hydrolysis back into AMP by phosphodiesterases (PDE). Treg express the two ectoenzymes that catabolize extracellular inflammatory ATP: CD39 and CD73. CD39 converts. ATP to ADP, then to AMP, which is subsequently converted into adenosine by CD73. Adenosine binds to cell surface adenosine receptors, which exist in several isoforms; the ligation of A2A isoform and A2B isoform has immunosuppressive effects. Upon binding of adenosine to adenosine receptors, adenylyl cylcase (AC) is activated, thereby resulting in cAMP production.

Figure 7:
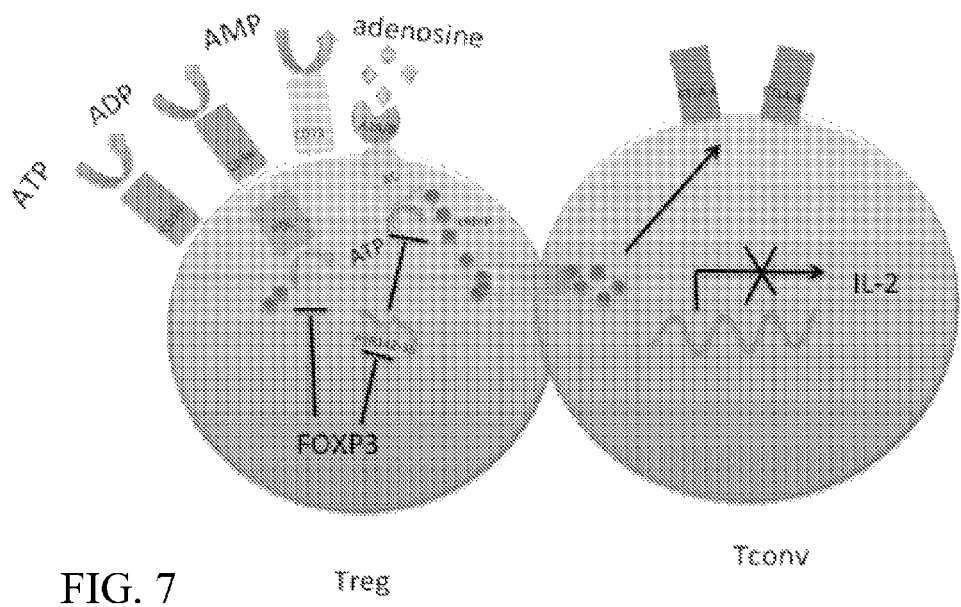
FIG. 7 shows one mechanism of suppression of APC/Teff by Treg mediated by adenosine metabolism. Pro-inflammatory extracellular ATP is metabolized to adenosine by ectoenzymes expressed by Treg; adenosine then binds GPCR (G protein couple receptor) adenosine receptors. The binding of adenosine to its receptor activates adenylyl cyclase (AC), which converts intracellular ATP to cAMP. cAMP, transferred via gap junctions to Teff and/or APCs, modulates cell proliferation, cytokine production, and expression of suppressive molecules. cAMP is degraded by phosphodiesterases (PDE), and the degradation of cAMP by PDE is regulated by FOXP3. FOXP3 also inhibits the degradation of AC mRNA by miR142-3p, and thus, increases the level of cAMP.

Meanwhile, the degradation of cAMP is inhibited FOXP3—the main Treg-specific transcription factor that directly inhibits the PDE3b isoform of phosphodiesterases. FOXP3 also downregulates miR-142-3p microRNA, which targets AC RNA for degradation. Accordingly, the level of cAMP remains elevated in Treg. The elevated cAMP level plays an important role in their suppressive activity. When transferred to target cells, cAMP upregulates inducible cAMP early repressor (ICER) transcription factor. The presence of ICER transcription factor and nuclear factor of activated T-cells (NFATs) suppresses IL-2 production. Also, cAMP upregulates the expression of the regulatory surface molecule cytotoxic I-Lymphocyte Antigen 4 (CTLA-4), which might play a role in infectious tolerance (FIG. 7).

Figure 8:
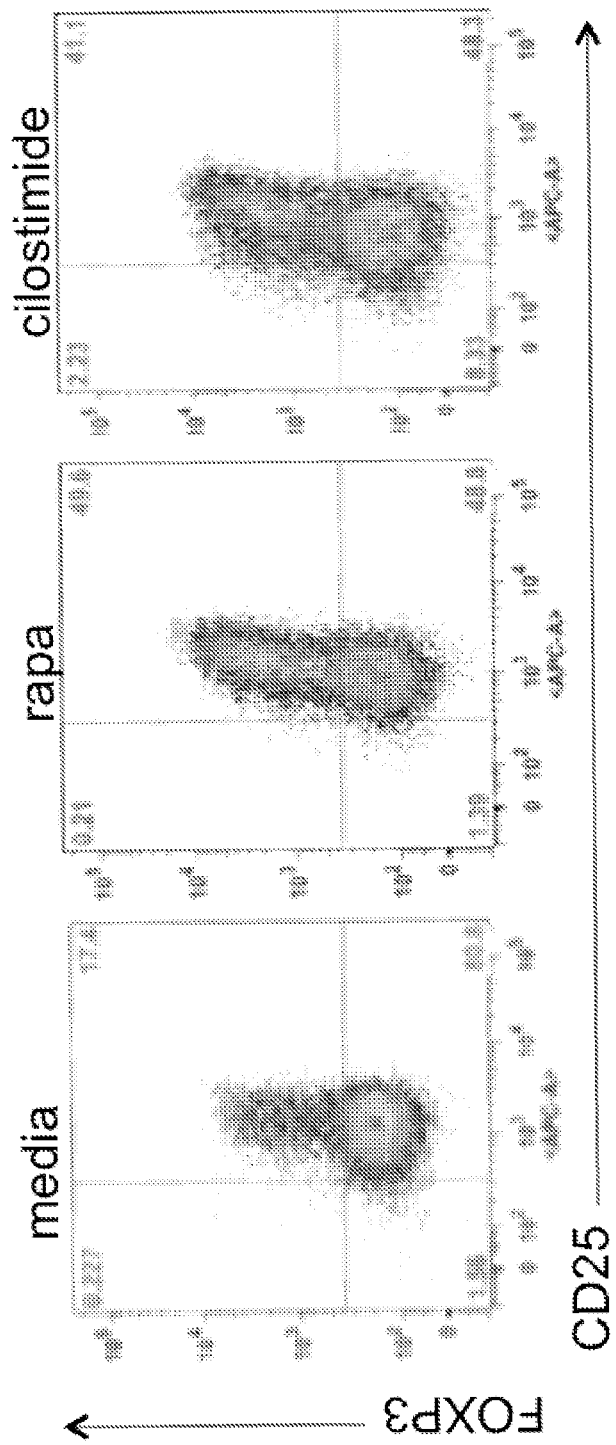
FIG. 8 shows that the inhibition of PDE induces FOXP3 expression in naïve human CD4+ T cells. Freshly isolated naïve (CD4+ CD25− CD127hi CD45RO−) T cells are cultured and treated with PDE3b and PDE4 inhibitors (middle panel) or rapamycin (positive control) (right panel), or are left untreated (left panel). CD25 and FOXP3 expression is measured by flow cytometry after 14 days of expansion.

Treatment of Tregs with small molecules that maintain high cAMP levels in T cells can be used to induce a regulatory phenotype. Small molecules that maintain high cAMP levels in T cells include agents that inhibit PDEs and agents that activate AC. As shown in FIG. 8, treatment of freshly isolated naïve CD4+ (CD4+ CD25− CD45RO−) T cells with cilostamide, a PDE3b inhibitor, results in increased FOXP3 induction, when compared to non-treated controls. The ratio of FOXP3+ cells in the cilostamide-treated group is comparable to that of the rapamycin-treated group (FIG. 8).

Figure 9:
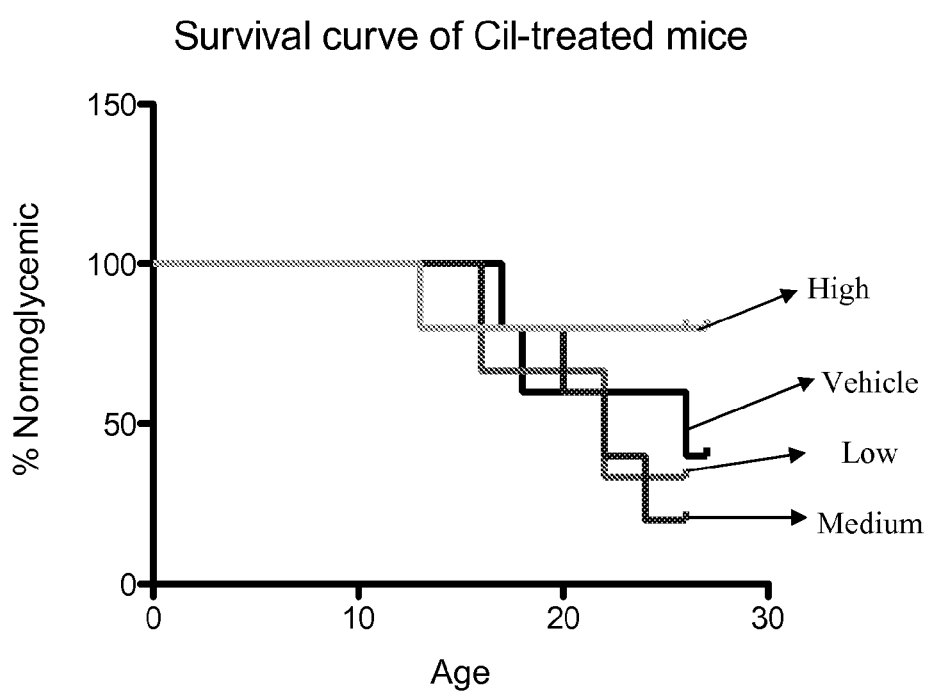
FIG. 9 shows that cilostamide injection delays the onset of diabetes in NOD mice. Briefly, 8-week old NOD mice are injected (i.p.) with various doses of cilostamide (low: 0.65 mg/kg, medium: 6.5 mg/kg, high: 65 mg/kg), or vehicle only. Cilostamide is administered three times a week for five weeks. The onset of diabetes in treated mice is monitored by blood glucose measurements. Diabetes is diagnosed if the blood glucose readings are greater than 240 mg/dl for two days.

The increase in level of FoxP3+ cells at an early stage of the autoimmune attack can be used to prevent or delay the onset of autoimmune disease. Briefly, 8-week old NOD mice are treated with various doses (low: 0.65 mg/kg; medium: 6.5 mg/kg; high: 65 mg/kg) of cilostamide via intraperitoneal (i.p.) injection. Cilostamide is administered to the mice three times a week for five weeks. The administration of cilostamide at a dose of 65 mg/kg, when utilized as a monotherapy, delayed the onset of diabetes in NOD mice (FIG. 9).

Example 4—Generation of Nanoparticle-Coupled Regulatory T Cells for Suppressing Pathogenic Autoreactive T Cell Responses in a Nod Mouse Model This Example describes nanoparticle (NP)-coupled Tregs capable of suppressing pathogenic autoreactive T cell responses in non-obese diabetic (NOD) mice. The nanoparticles are made of bio-degradable polymeric material poly-lactic-co-glycolic acid) (PLGA), and encapsulate therein a vaccine composition comprising IL-2 (a Treg selective growth factor), insulin B chain$_{(9-23)}$ peptide (an autoantigen), and rapamycin (an mTOR inhibitor).

PLGA-NPs with different concentrations of IL-2 and rapamycin are generated. NPs are incubated with activated mouse or human CD4$^+$ T cells. The optimal concentrations of IL-2 and rapamycin for upregulating FoxP3 and/or limiting Teff cell proliferation are determined.

The conjugation of NPs to the surface of Tregs is optimized by linking fluorescently labeled PLGA-NPs to the surface of in vitro expanded Tregs. The in vitro functionality of NP-conjugated Treg cells is monitored based on expression of phenotypic markers such as helios and FoxP3, as well as Treg cell proliferation, cell signaling, and viability.

The therapeutic effects of the vaccine-loaded NPs for preventing and treating diabetes are evaluated. Briefly, eight-week-old female NOD mice are randomly separated into the following groups (n=15/group): mice receiving no treatment, mice receiving NPs alone, mice receiving NPs loaded with the vaccine composition containing IL-2, the insulin B chain$_{(9-23)}$ peptide, and rapamycin, mice receiving Tregs alone, mice receiving Tregs conjugated with empty NPs, and mice receiving Tregs conjugated with vaccine-loaded NPs. In each group, ten mice are included in a cohort for Kaplan-Meir analysis, while the remaining five mice are used for cross-sectional mechanistic studies.

The treatment effects are determined using data generated from immunophenotyping by fluorescence-activated cell sorting (FACS), gene expression, pancreatic histology, insulitis scoring, hematology, and in vitro functional assays. ELISpot assays are employed to evaluate antigen-specific cell responses of intracellular cytokines (e.g., IFN-γ, IL-17, IL-10).

Among the different treatment groups, the greatest efficacy for treating diabetes is observed in NOD mice transferred with Tregs conjugated with NPs loaded with the vaccine composition containing antigen, IL-2, and rapamycin. Specifically, the transfer of vaccine-loaded NP-conjugated Tregs results in a robust expansion of antigen-specific Tregs for immune protection. The short-term therapeutic efficacy is achieved by the transferred Treg population, whereas the long-term tolerance results from the development of endogenous Tregs.

To determine the precise mechanism of the vaccine-loaded, NP-conjugated T cells in reversing autoimmunity, one group of mice is treated with anti-Thy1.1 antibody, thereby only depleting the Treg cells that were transplanted to the mice via the adoptive Treg therapy. Another group of mice is treated with anti-CD25 treatment using PC62 mAb, thereby depleting the total Treg population. It is postulated that only following depletion of the total Treg population is immune tolerance lost; this indicates that the transfer of the vaccine-loaded NP-conjugated Treg cells expands endogenous Treg population.

Example 5—Development of Human Nanoparticle-Conjugated Regulatory T Cells

In this Example, CD4$^+$CD45RA$^+$CD127$^{-/lo}$CD25$^+$ T cells obtained from peripheral blood or umbilical cord blood are sorted by FACS, and are expanded in vitro. The in vitro expanded Tregs are separated into the following groups: 1) unconjugated Tregs, 2) Tregs conjugated with empty NPs, 3) Tregs conjugated with NPs loaded with IL-2, 4) Tregs conjugated with NPs loaded with rapamycin, and 5) Tregs conjugated with NPs loaded with IL-2 and rapamycin.

In each group, the Tregs are cultured in fresh IL-2-deficient media, and allowed to expand in cell culture for a time-course experiment. Treg cells are harvested at 24, 48, 72, and 96 hr post culture, and are assessed for cell viability, expression of phenotypic markers (e.g., CD25, CD127, FOXP3, and helios) and intracellular cytokines (e.g., IL-2, IL-10, IFN-γ).

Epigenetic modifications at the FOXP3 Treg-specific demethylated region, which have been shown to correlate with Treg function (Polansky et al. (2008), Wieczorek et al. (2009)), are assessed (Epiontis, Germany). Tregs are monitored for their capacity to suppress proliferation of responding T cells.

The NP-conjugated Tregs are carboxyfluorescein diacetate succinimidyl ester (CFSE) labeled and mixed with fresh CD4$^+$CD45RACD127$^+$CD25$^-$ Tconv cells (labeled with violet dye) at various ratios (1:0, 1:1, ½:1, 0:1). The Treg cultures are restimulated in vitro and assessed for proliferation and expression of various phenotypic markers such as CD25, CD127, FOXP3, and helios. The autocrine and paracrine effects of the NP-conjugated vaccines on Tregs and Tconv cells are determined.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

Lowe, C. E., Cooper, J. D., Brusko, T., Walker, N. M., Smyth, D. J., Bailey, R., Bourget, K., Plagnol, V., Field, S., Atkinson, M., et al. 2007. Large-scale genetic fine mapping and genotype-phenotype associations implicate polymorphism in the IL2RA region in type 1 diabetes. *Nat Genet.*

Long, S. A., Cerosaletti, K., Bollyky, P. L., Tatum, M., Shilling, H., Zhang, S., Zhang, Z. Y., Pihoker, C., Sanda, S., Greenbaum, C., et al. 2010. Defects in IL-2R signaling contribute to diminished maintenance of FOXP3 expression in CD4(+)CD25(+) regulatory T-cells of type 1 diabetic subjects. *Diabetes* 59:407-415.

Rieck, M., Arechiga, A., Onengut-Gumuscu, S., Greenbaum, C., Concannon, P., and Buckner, J. H. 2007. Genetic variation in PTPN22 corresponds to altered function of T and B lymphocytes. *J Immunol* 179:4704-4710.

Smyth, D. J., Plagnol, V., Walker, N. M., Cooper, J. D., Downes, K., Yang, J. H., Howson, J. M., Stevens, H., McManus, R., Wijmenga, C., et al. 2008. Shared and distinct genetic variants in type 1 diabetes and celiac disease. *N Engl J Med* 359:2767-2777.

Brusko, T. M., Putnam, A. L., and Bluestone, J. A. 2008. Human regulatory T cells: role in autoimmune disease and therapeutic opportunities. *Immunol Rev* 223:371-390.

Jonuleit, H., Schmitt, E., Kakirman, H., Stassen, M., Knop, J., and Enk, A. H. 2002. Infectious tolerance: human CD25(+) regulatory T cells convey suppressor activity to conventional CD4(+) T helper cells. *J Exp Med* 196:255-260.

Battaglia, M., Stabilini, A., Migliavacca, B., Horejs-Hoeck, J., Kaupper, T., and Roncarolo, M. G. 2006. Rapamycin promotes expansion of functional CD4+CD25+FOXP3+ regulatory T cells of both healthy subjects and type 1 diabetic patients. *J Immunol* 177:8338-8347.

Riley, J. L., June, C. H., and Blazar, B. R. 2009. Human T regulatory cell therapy: take a billion or so and call me in the morning. *Immunity* 30:656-665.

Scalapino, K. J., Tang, Q., Bluestone, J. A., Bonyhadi, M. L., and Daikh, D. I. 2006. Suppression of disease in New Zealand Black/New Zealand White lupus-prone mice by adoptive transfer of ex vivo expanded regulatory T cells. *J Immunol* 177:1451-1459.

Kohm, A. P., Carpentier, P. A., Anger, H. A., and Miller, S. D. 2002. Cutting edge: CD4+CD25+ regulatory T cells suppress antigen-specific autoreactive immune responses and central nervous system inflammation during active experimental autoimmune encephalomyelitis. *J Immunol* 169:4712-4716.

Mottet, C., Uhlig, H. H., and Powrie, F. 2003. Cutting edge: cure of colitis by CD4+CD25+ regulatory T cells. *J Immunol* 170:3939-3943.

Polansky, J. K., Kretschmer, K., Freyer, J., Floess, S., Garbe, A., Baron, U., Olek, S., Hamann, A., von Boehmer, H., and Huehn, J. 2008. DNA methylation controls Foxp3 gene expression. *Eur J Immunol* 38:1654-1663.

Wieczorek, G., Asemissen, A., Model, F., Turbachova, I., Floess, S., Liebenberg, V., Baron, U., Stauch, D., Kotsch, K., Pratschke, J., et al. 2009. Quantitative DNA methylation analysis of FOXP3 as a new method for counting regulatory T cells in peripheral blood and solid tissue. *Cancer Res* 69:599-608.

We claim:

1. A method for inducing immune tolerance in a subject wherein the method comprises the steps of:
   obtaining autologous regulatory T cells (Tregs) from a human subject;
   encapsulating into bio-degradable nanoparticles a Treg selective growth factor selected from IL-2, rapamycin, cilostamide, milrinone, amrinone, cilomilast, rolipram, theophylline, and pentoxifylline; and an autoantigen;
   surface-conjugating the nanoparticles to the autologous Tregs; and
   administering the nanoparticle-conjugated Tregs to the subject;
   wherein the nanoparticle-conjugated Tregs act in an autocrine and paracrine fashion to induce immune tolerance, and
   wherein the autoantigen is of an insulin peptide, an islet cell autoantigen, glutamic acid decarboxylase (GAD), insulinoma-associated-2-protein (IA-2), or preproinsulin.

2. The method, according to claim 1, wherein the bio-degradable material comprises poly(lactide-co-glycolide) (PLGA).

3. The method, according to claim 1, wherein the nanoparticle encapsulates a Treg selective growth factor selected from IL-2, rapamycin, and cilostamide.

4. The method, according to claim 3, wherein the nanoparticle encapsulates IL-2 and cilostamide.

5. The method, according to claim 1, wherein the subject has type 1 diabetes.

6. The method, according to claim 1, wherein the nanoparticle has a size of about 300 to 500 nanometers in diameter.

7. A method of treating or delaying the onset of type I diabetes, wherein the method comprises the steps of:
   obtaining autologous regulatory T cells (Tregs) from a human subject;
   encapsulating into bio-degradable nanoparticles a Treg selective growth factor selected from IL-2, rapamycin, cilostamide, milrinone, amrinone, cilomilast, rolipram, theophylline, and pentoxifylline; and an autoantigen;
   surface-conjugating the nanoparticles to the autologous Tregs; and
   administering the nanoparticles-conjugated Tregs to the subject;
   wherein the nanoparticle-conjugated Tregs act in an autocrine and paracrine fashion to induce immune tolerance; and
   the autoantigen is an insulin peptide, an islet cell autoantigen, glutamic acid decarboxylase GAD), insulinoma-associated-2-protein (IA-2), or preproinsulin.

8. The method, according to claim 7, wherein the bio-degradable material comprises poly(lactide-co-glycolide) (PLGA).

9. The method, according to claim 7, wherein the nanoparticle encapsulates a Treg selective growth factor selected from IL-2, rapamycin, and cilostamide.

10. The method, according to claim 9, wherein the nanoparticle encapsulates IL-2 and cilostamide.

11. The method, according to claim 7, wherein the subject has type 1 diabetes or has a family history of type 1 diabetes.

12. A nanoparticle-coupled tolerogenic Treg cell therapeutic composition comprising:
   a) nanoparticles made of bio-degradable material, wherein the nanoparticles encapsulate therein a Treg selective growth factor selected from IL-2, rapamycin, cilostamide, milrinone, amrinone, cilomilast, rolipram, theophylline, and pentoxifylline; and an autoantigen; and
   b) a population of autologous or allogeneic Treg cells;
   wherein the Treg cells are surface-conjugated with the nanoparticle; and
   wherein the autoantigen is an insulin peptide, an islet cell autoantigen, glutamic acid decarboxylase (GAD), insulinoma-associated-2-protein (IA-2), or preproinsulin.

13. The composition, according to claim 12, wherein the bio-degradable material comprises poly(lactide-co-glycolide) (PLGA).

14. The composition, according to claim 12, wherein the Treg selective growth factor is IL-2, rapamycin, or cilostamide.

* * * * *

UNITED STATES PATENT AND TRADEMARK OFFICE
CERTIFICATE OF CORRECTION

PATENT NO.        : 9,913,830 B2
APPLICATION NO.   : 14/241228
DATED             : March 13, 2018
INVENTOR(S)       : Todd M. Brusko et al.

Page 1 of 1

It is certified that error appears in the above-identified patent and that said Letters Patent is hereby corrected as shown below:

In the Specification

Column 1,
Line 52, "transferred. Tregs" should read -- transferred Tregs --.

Column 2,
Lines 48-49, "$CD4^+CD45RA^+CD25^+CD127^{31^{l/o}}$" should read
-- $CD4^+CD45RA^+CD25^+CD127^{-l/o}$ --.

Column 10,
Line 45, "I-Lymphocyte" should read -- T-Lymphocyte --.

Column 12,
Line 22, "$CD4^+CD45RACD127^+CD25^-$" should read -- $CD4^+CD45RA^+CD127^+CD25^-$ --.

Signed and Sealed this
Twenty-fourth Day of July, 2018

Andrei Iancu
*Director of the United States Patent and Trademark Office*